(12) United States Patent
Clark

(10) Patent No.: US 6,606,994 B1
(45) Date of Patent: Aug. 19, 2003

(54) AUTOMATIC VENTILATOR WATER TRAP EVACUATOR

(76) Inventor: Bradley R. Clark, 6797 E. Hwy. 12, Lodi, CA (US) 95240

( * ) Notice: Subject to any disclaimer, the term of this patent is extended or adjusted under 35 U.S.C. 154(b) by 0 days.

(21) Appl. No.: 09/556,445

(22) Filed: Apr. 24, 2000

(51) Int. Cl.[7] .............................. A62B 19/00; A61M 1/00
(52) U.S. Cl. ............................ 128/205.12; 128/204.18; 604/317
(58) Field of Search ..................... 128/204.18, 204.21, 128/204.22, 204.24, 205.12, 205.24, 205.27, 206.22; 604/317, 318, 319, 313, 320, 316, 322, 327, 328

(56) References Cited

U.S. PATENT DOCUMENTS

| | | | | |
|---|---|---|---|---|
| 3,603,313 A | * | 9/1971 | Arblaster | 128/205.12 |
| 3,682,166 A | * | 8/1972 | Jacobs | 128/205.19 |
| 3,719,197 A | * | 3/1973 | Pannier et al. | 137/205 |
| 4,197,858 A | * | 4/1980 | Osborn | 600/531 |
| 4,327,718 A | * | 5/1982 | Cronenberg | 128/205.12 |
| 4,382,806 A | | 5/1983 | Hakala | |
| 4,391,271 A | | 7/1983 | Blanco | |
| 4,417,574 A | * | 11/1983 | Talonn et al. | 128/205.12 |
| 4,456,008 A | | 6/1984 | Clawson | |
| 4,465,485 A | * | 8/1984 | Kashmer et al. | 128/205.12 |
| 4,558,696 A | | 12/1985 | Eiserman | |
| 4,678,488 A | | 7/1987 | Howard | |
| 4,727,871 A | * | 3/1988 | Smargiassi et al. | 128/204.17 |
| 4,739,786 A | * | 4/1988 | Parkinson | 137/2 |
| 4,867,153 A | * | 9/1989 | Lorenzen et al. | 128/205.12 |
| 5,072,737 A | * | 12/1991 | Goulding | 128/204.23 |
| 5,119,807 A | | 6/1992 | Roberts | |
| 5,168,868 A | * | 12/1992 | Hicks | 128/205.12 |
| 5,228,436 A | * | 7/1993 | Parkin | 128/203.12 |
| 5,388,571 A | * | 2/1995 | Roberts et al. | 128/200.18 |
| 5,394,881 A | * | 3/1995 | Block, Jr. | 128/205.12 |
| 5,398,677 A | * | 3/1995 | Smith | 128/205.12 |
| 5,433,194 A | * | 7/1995 | Fry | 128/205.12 |
| 5,458,138 A | * | 10/1995 | Gajo | 128/205.12 |
| 5,640,951 A | * | 6/1997 | Huddart et al. | 128/203.26 |
| 5,711,296 A | * | 1/1998 | Kolobow | 128/204.28 |
| 5,722,393 A | * | 3/1998 | Bartel et al. | 128/204.15 |
| 5,960,837 A | * | 10/1999 | Cude | 137/205 |
| 5,975,165 A | * | 11/1999 | Motosugi et al. | 141/392 |
| 6,131,571 A | * | 10/2000 | Lampotang et al. | 128/204.18 |

FOREIGN PATENT DOCUMENTS

GB 2224957 * 5/1990

* cited by examiner

*Primary Examiner*—Weilun Lo
*Assistant Examiner*—Teena Mitchell
(74) *Attorney, Agent, or Firm*—Heisler & Associates

(57) ABSTRACT

A system 10 is provided for automatically evacuating a water trap 50 of a ventilator 20. The ventilator 20 delivers air through a humidifying water heater 30 and along an air supply line 40 to a patient requiring breathing assistance. A dip 44 in the air supply line 40 is configured with a water trap 50 for collecting condensate within the air supply line 40. A suction line 60 is located within the water trap 50 at a tip 62 and has an end 68 outside of the water trap 50 which is coupled to a canister 70. The canister 70 is also coupled to a vacuum source 100 through a valve 80. When the valve 80 is in a first open position, the vacuum source 100 provides suction along the suction line 60 so that liquids collecting within the water trap 50 are evacuated out of the water trap 50 and delivered into the canister 70. A controller 90 controls the frequency with which the valve 80 is opened and a duration for which the valve 80 remains in the opened position. In one form of the invention, a water level probe 114 can also be provided within the water trap 50 which communicates to the controller 90 information relating to a level of fluid contained within the water trap 50. Manually adjustable input devices can also be provided on the controller 90 for adjusting the frequency and duration with which the valve 80 remains in the open position. The water trap 50 is thus periodically automatically evacuated.

8 Claims, 4 Drawing Sheets

US 6,606,994 B1

AUTOMATIC VENTILATOR WATER TRAP EVACUATOR

FIELD OF THE INVENTION

The following invention relates to systems for evacuating water from water traps used in ventilator systems that assist patients with the breathing function. More specifically, this invention relates to automatic water trap evacuators that suction water from the water trap into a larger canister automatically and without the need for human intervention.

BACKGROUND OF THE INVENTION

In the breathing ventilator system arts, an array of devices have been devised to provide warm, moist air to a patient while preventing blocking of air supply lines with condensed moisture or ingestion of condensed moisture (i.e. water). These devices remove water from the air delivery tubes and collect the water in containers commonly referred to as water traps. The water accumulates in the water traps until the water reaches the limited capacity of the trap. A capacity of the trap is generally reached in about one to one and a half hours. Typically, the trap is then emptied by a hospital staff member or other care giver.

The prior art has several drawbacks that range from inconvenience to danger to the patients. First, failure to empty the water trap could lead to blockage of the air supply line or to the patient ingesting water into his or her lungs, posing a danger to the patient's physical well being. Second, the patient may experience difficulty breathing if the water trap becomes full or overflows. Third, the patient is typically awakened every hour or two during the night while the trap is being emptied. Fourth, the patient may experience apprehension over whether or not the trap will in fact be emptied, particularly if the patient has had prior unpleasant experiences. Finally, a care giver may spend substantial amounts of time emptying traps on a regular basis, when this time could be more productively spent on other tasks.

Accordingly, a need exists for a system that minimizes or eliminates the need for human intervention and the aforestated problems associated therewith.

SUMMARY OF THE INVENTION

The automatic water trap evacuator of this invention solves the problems associated with care givers emptying the traps as in the prior art. Specifically, the evacuator incorporates design features that address the problems as a whole. These design features automate the water evacuation process so that no care giver intervention is required. A central vacuum suction system pulls the water from the water trap into a canister by way of a series of interconnecting design features. A suction line is inserted into the water trap at one end and connected to a large canister at the other end. The suction line provides a path between the water trap and the canister where the evacuated water is stored. The canister is connected to a suction source through a valve. The valve is positioned by a controller that is powered by a low voltage power source, such as a 12 volt (or lower) transformer coupled to an AC 110 volt standard electric power outlet.

A typical use of the evacuator occurs as follows. The evacuator and ventilator systems are interconnected and the ventilator connected to the patient in typical prior art fashion. The vacuum source is connected to a valve outflow. The ventilator system supplies humidified, warm air to the patient while the water trap collects the moisture that condenses in the tubing and flows into the trap.

The valve remains closed for a predetermined amount of time while the water level in the trap rises. After the predetermined time has elapsed, the controller opens the valve. The frequency of valve opening preferably can be adjusted. The suction causes the water to be pulled from the water trap into the canister. Typically, this might occur every hour. The controller keeps the valve open for a predetermined amount of time, typically five seconds. The duration of the valve's open status preferably can be adjusted. The water is evacuated, thereby preventing overflow and a need for human intervention. The process is repeated indefinitely.

An optional feature of the evacuator is a sensor that is inserted into the water trap and connected to the controller. The sensor indicates the water level in the water trap. The controller would open the valve when the water reaches a certain predetermined level, and will close the valve when the water reaches a certain predetermined lower level, as indicated by the sensor.

OBJECTS OF THE INVENTION

Accordingly, a primary object of the present invention is to automate the water trap evacuation process associated with ventilators that have heaters.

Another object of the present invention is to evacuate the water trap repeatedly over prolonged periods of time, such as when the patient is sleeping.

Another object of the present invention is to protect the patient from breathing difficulties that may arise if the water trap becomes too full.

Another object of the present invention is to prevent the patient from ingesting water into his or her lungs if the water trap overflows.

Another object of the present invention is to reduce patient apprehension that the water trap may not be timely emptied.

Another object of the present invention is to reduce interference with patient's sleep that may result from manual evacuation of the water trap.

Another object of the present invention is to reduce the work load of hospital staff personnel by reducing the amount of time required to attend the ventilator system.

Another object of the present invention is to help make scheduling of hospital personnel more flexible by eliminating the need for hourly evacuation of the water traps for each patient using a ventilator.

Other further objects of the present invention will become apparent from a careful reading of the included drawing figures, the claims and detailed description of the invention.

DESCRIPTION OF THE PREFERRED EMBODIMENT

Figure 2:
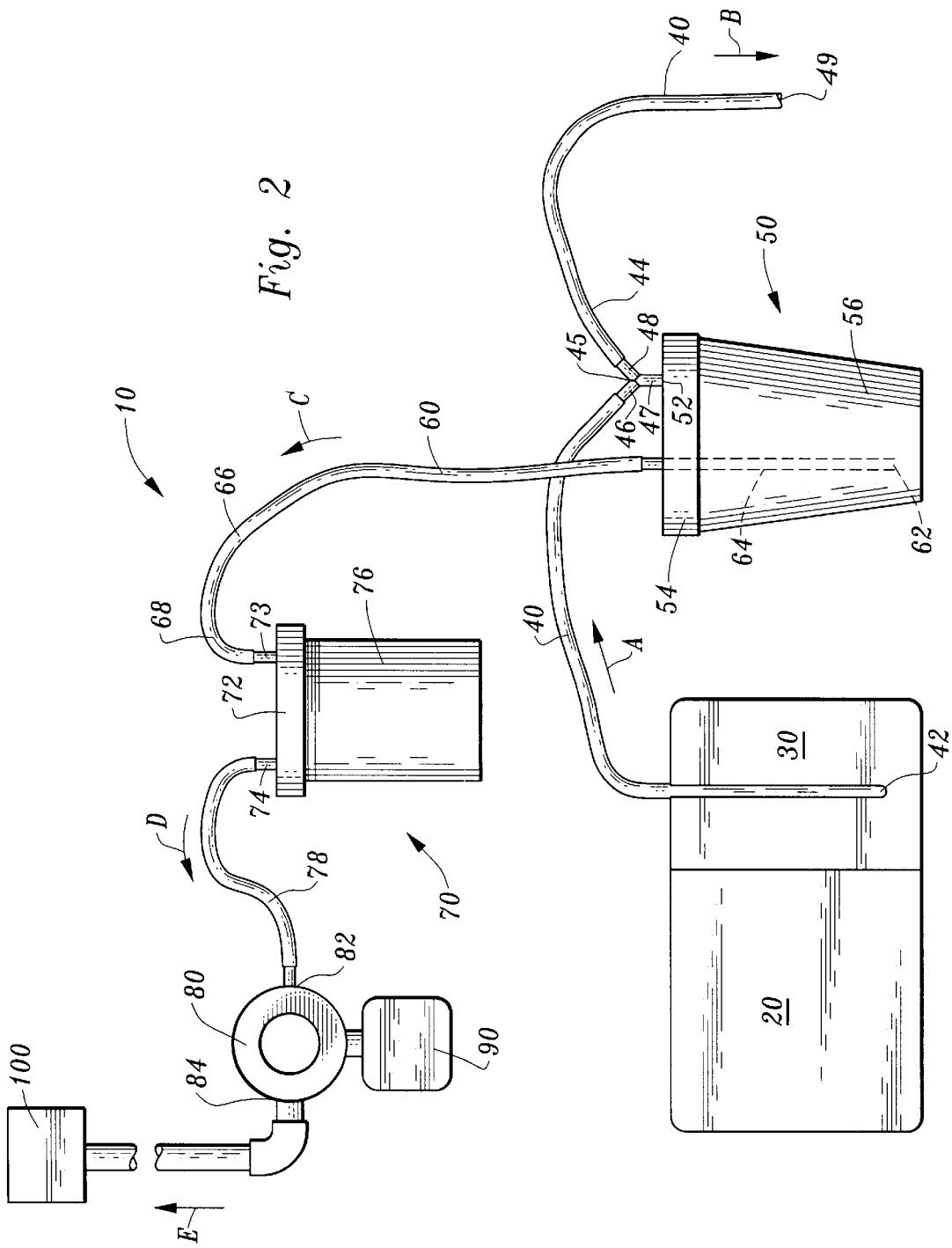
FIG. 2 is a schematic arrangement of this invention interconnected to a ventilator, heater and water trap, including a canister for collecting evacuated liquids, a controller for initiating and stopping liquid evacuation, and a vacuum source for pulling the liquid into the canister.

Referring to the drawings, wherein like reference numerals represent like parts throughout the various drawing figures, reference numeral 10 is directed to a system for automatically evacuating fluids from a water trap 50 of a ventilator 20 (FIG. 2). The system 10 thus eliminates the necessity of having personnel manually empty the water trap 50 around the clock.

Figure 1:
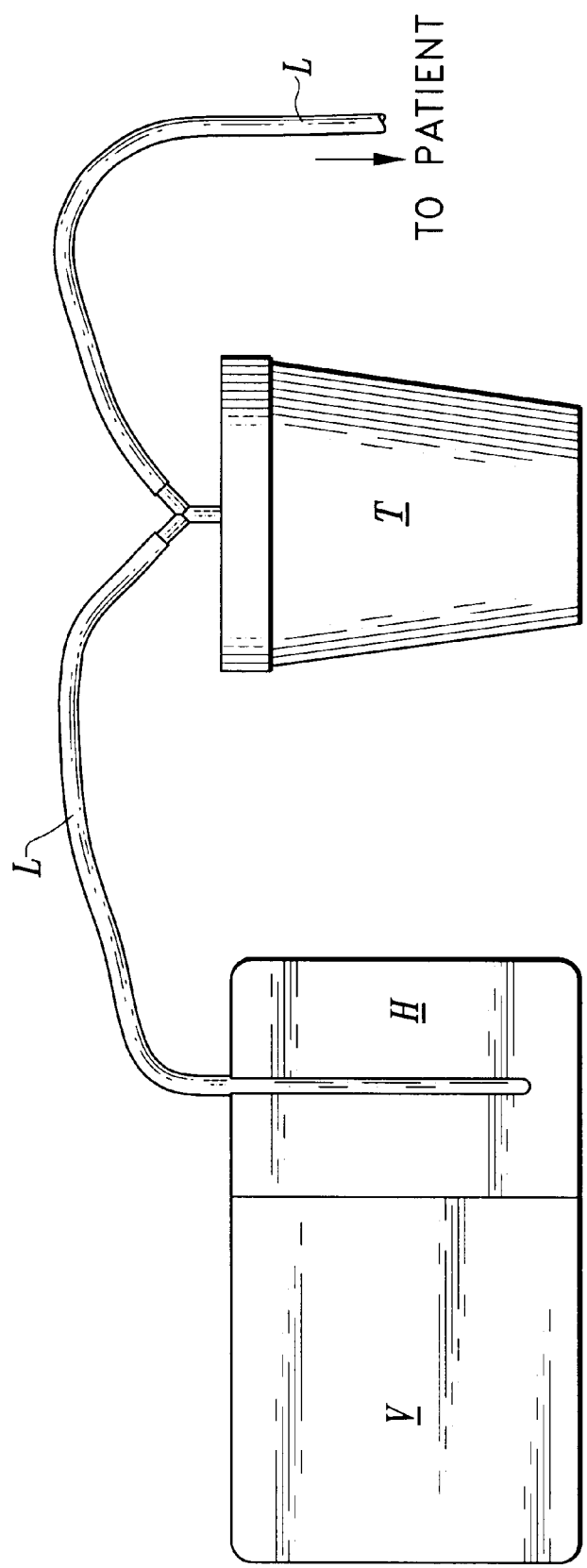
FIG. 1 is a schematic of a prior art ventilator heater and water trap as they are typically interconnected.

In essence, and with particular reference to FIGS. 1 and 2, details of the prior art ventilator V and water trap T and the improvement provided by the system 10 of this invention are described. The ventilator V, known in the prior art, acts as a pump to deliver air to a patient which requires breathing assistance. The ventilator V can optionally additionally assist the patient with exhalation of air. Ventilators V typically include a water heater H which heats water which moisturizes air exiting the ventilator V before the air passes along a line L leading up to the patient. While this moisture desirably elevates the humidity of the air delivered to the patient, it undesirably results in condensation along the air supply line L. To remove such condensation, a low point in the air supply line L is provided with a water trap T. Water and other fluids, which may be discharged from the patient and travel along the air supply line L, collect within the water trap T and then can be periodically removed by medical personnel.

With the improvement of this invention (FIG. 2) the ventilator 20 delivers air moisturized by the water heater 30 along air supply line 40 to the patient just as in the prior art. A water trap 50 is similarly located at a dip 44 in the air supply line 40 to collect condensed moisture and other liquids within the air supply line 40. Uniquely, a suction line 60 extends down into the water trap 50 and is coupled to a vacuum source 100 so that liquids collecting within the water trap 50 can be removed from the water trap 50 automatically, by being sucked out along the suction line 60. A canister 70 is provided along the suction line 60 to collect the liquids removed from the water trap 50. The canister 70 is larger than the water trap 50 and is not directly in the line between the patient and the ventilator 20 so that the canister 70 can be emptied without disrupting operation of the ventilator 20. A valve 80 is also interposed along the suction line 60 to selectively cause the suction line 60 to evacuate the water trap 50 only periodically as necessary. A controller 90 is provided which controls the opening and closing of the valve 80.

More specifically, and with particular reference to FIG. 2, details of the automatic ventilator water trap evacuator system 10 of this invention are described. The ventilator 20 can be any form of prior art ventilator capable of delivering air or other breathable fluids to the patient. Typically, the ventilator 20 would additionally include a water heater 30 for moisturizing the air delivered by the ventilator 20. This air is delivered along an air supply line 40, (along arrow A) where it eventually arrives at the patient, (along arrow B).

The air supply line 40 includes an entrance 42 within the ventilator 20 where air first enters the air supply line 40. A dip 44 in the air supply line 40 defines a lowest point in the air supply line 40 between the ventilator 20 and the patient.

A junction 45 is located at this dip 44. The junction 45 has three arms and is preferably configured in the form of a "Y" with an inlet arm 46 closest to the ventilator 20, a condensate arm 47 extending down from a center of the junction 45 and an outlet arm 48 closest to an exit 49 of the air supply line 40 adjacent the patient. The condensate arm 47 extends down into the water trap 50.

The water trap 50 is preferably configured to include an inlet 52 coupled to the condensate arm 47 which passes through a cap 54 which attaches to a cup 56 of the water trap 50. Preferably, the cap 54, water trap 50 and junction 45 are all formed as a single piece or separate pieces that are permanently joined together. The entire water trap 50 is preferably sufficiently light in weight that it does not require support other than being suspended along the air supply line 40. The water trap 50 is preferably sufficiently heavy that it can itself cause its location to be the lowest point in the air supply line 40 between the ventilator 20 and the exit 49 adjacent the patient. Within these weight parameters, it is typically desirable that the water trap 50 be as large as possible so that it does not require evacuation as often. However, the water trap 50 cannot be excessively large or it will be too heavy to be supported by the air supply line 40, especially when full of liquids. The cap 54 is preferably not removable from the cup 56 and the inlet 52 preferably passes through the cap 54.

The suction line 60 preferably extends through the cap 54 and down to a tip 62 adjacent to a lowermost portion of the cup 56. The top 62 is sufficiently low that it is almost always submerged in liquid and does not disrupt flow along the air supply line 40. The suction line 60 thus has an interior portion 64 within the water trap 50 and an exterior portion 66 outside of the water trap 50. The exterior portion 66 leads up to an end 68 adjacent the canister 70.

The canister 70 is preferably mounted on a wall adjacent the patient's bed. The canister 70 can be significantly larger than the water trap 50 due to its ability to easily rest upon a supported surface. The canister 70 includes a lid 72 which includes an inlet support 73 therein and an outlet support 74 therein. The outlet support 73 interfaces with the end 68 of the suction line 60 so that the suction line 60 can readily feed fluids from a water trap 50 into the canister 70. The outlet support 74 supports an outlet tube 78 which extends to the valve 80. A reservoir 76 is removably attachable to the lid 72 for convenient disposal of liquids which have collected within the reservoir 76 of the canister 70. Alternatively, the canister 70 can include some other form of outlet, such as a discharge hole for emptying of the reservoir 76, and the reservoir 76 can be more permanently attached to the lid 72. However, the canister is preferably disposable and replaced with a new canister periodically.

It is desirable that the canister 70 be sufficiently large that it merely need be replaced on a daily basis or less often. Because the canister is not directly attached to the air supply line 40, and because the tip 62 of the suction line 60 is sufficiently low within the water trap 50 that it remains submerged within liquids remaining within the water trap 50, removal of the reservoir 76 from the lid 72 of the canister 70 does not disrupt the function of the ventilator 20 in any way, unlike when the prior art water trap T is being emptied. Of course, the suction line 60 cannot be used to evacuate the water trap 50 while the reservoir 76 of the canister 70 has been removed from the lid 72 for changing. This disruption of the suction line 60 has no impact on the patient because it does not disrupt air flow from the ventilator 20.

Fluids evacuated from the water trap 50 travel along the suction line 60, (along arrow C) and pass into the reservoir 76 of the canister 70. The valve 80 is normally closed. The central vacuum or suction system 100 is typically already available at a hospital type location for the system 10. An outflow port 84 of the valve 80 connects to the vacuum source 100. An inflow port 82 connects to the canister 70. The valve 80 is preferably solenoid actuated. Fluids (typically gases only) exiting the canister 70, (along arrow D) pass along the outlet tube 78 and into the inflow port 82 of the valve 80. The fluids then pass out of the outflow port 84 and on to the vacuum source 100 (along arrow E). The vacuum generated within the canister 70 draws liquids from the water trap 50, emptying the water trap 50. When the canister 70 is full it is replaced with a new one.

A controller 90 controls when the valve 80 will open. Preferably, the controller 90 is in the form of an adjustable timer with separate manual adjustability for the frequency with which the valve 80 toggles from the closed position to the open position and separate manual adjustability for a duration for which the valve 80 remains in the first open position before it returns to the second closed position.

Most preferably, the frequency with which the valve 80 is opened is every hour. However, depending on the settings of the ventilator 20, the humidity of the air and other atmospheric and ventilator 20 specific details, the frequency would often range between 0.5 hours and 2.0 hours. The range could be even greater in more unusual operating circumstances.

The duration for which the valve 80 remains in the first open position would typically be five seconds. This duration is essentially the amount of time necessary for the water trap 50 to be emptied. It is undesirable that the valve 80 remain in the first open position when the water trap 50 is empty, because air from the ventilator 20 intended for the patient would instead be sucked through the suction line 60 and on to the vacuum source 100. While briefly tolerable, it is undesirable for this condition to occur for more than a few seconds. If the water trap 50 is larger or if the power of the vacuum source 100 is less, the duration that the valve 80 should remain in the first open position would necessarily need to be increased. In typical operation, a duration of five seconds is appropriate. In less common circumstances, this duration might be reduced to as little as two seconds or as much as ten seconds. In rare instances, the duration that the valve 80 remains in the first open position could be reduced to less than two seconds or extended to greater than ten seconds, depending on the particular equipment being utilized and the amount of time necessary to fully evacuate the water trap 50.

Figure 5:
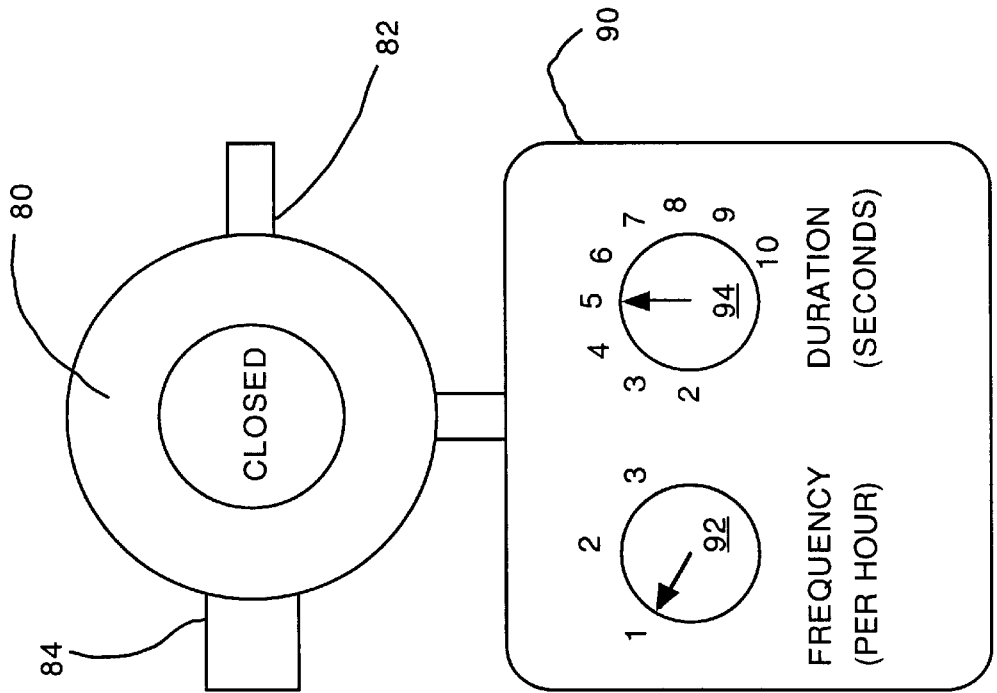
FIG. 5 is a detail similar to that which is shown in FIG. 4 but with the valve shown in the closed position.
Figure 4:
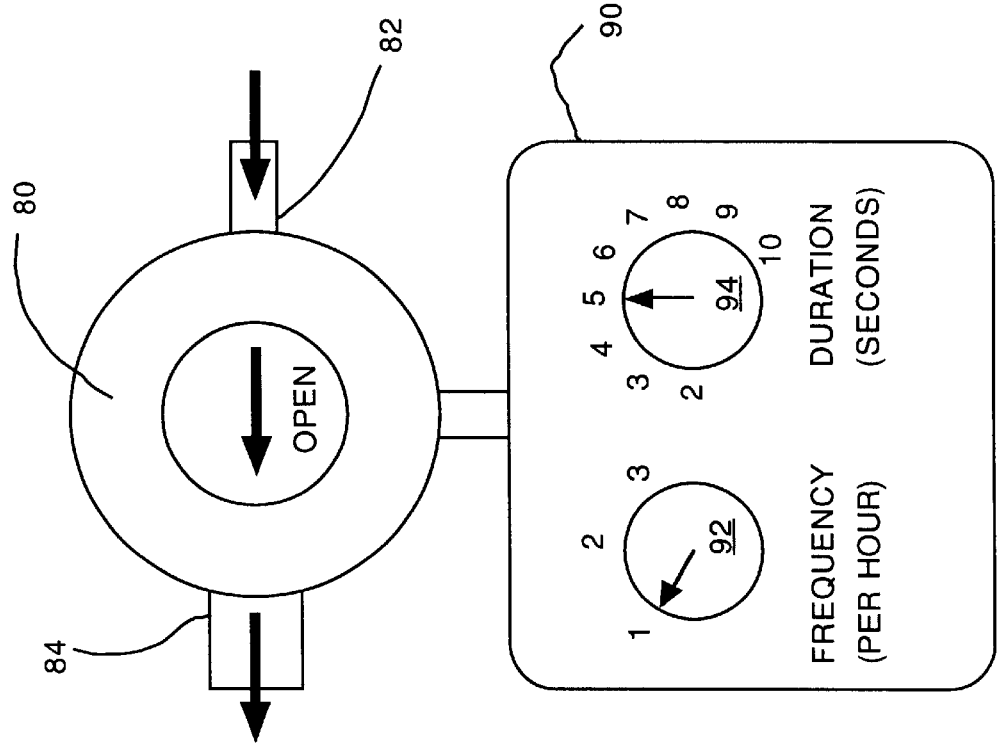
FIG. 4 is a detail of a portion of that which is shown in FIG. 2 particularly showing the valve and controller of this invention with the valve shown in the open position.

Preferably the controller 90 (FIGS. 4 and 5) includes two manually adjustable dials with one dial 92 manually adjustable to set the frequency with which the valve 80 toggles from the second closed position to the first open position. The second dial 94 would be used to manually select the duration for which the valve 80 remains in the first open position before returning to the second closed position. The dials could be provided with detents at the preferred one hour frequency and five second duration points. Alternatively, the controller 90 could be configured with an LCD display and appropriate up and down buttons for adjusting the frequency and duration for the operation of the valve 80. The controller 90 preferably additionally includes a manual override button which can be depressed by an operator to automatically cause the valve 80 to toggle from the second closed position to the first open position. Similarly, the same or a separate override button could be provided to allow the user to directly cause the valve 80 to toggle from the first open position to the second closed position.

The controller 90 could conceivably be configured to operate off of springs in a wind-up fashion or otherwise be configured non-electrically. However, the controller 90 preferably is a low voltage electrical device which is powered from a standard 110 volt AC outlet through a transformer which conditions the voltage to low voltage, such as 12 volt or more. In this way, should the device somehow short out, insufficient voltage would be present to create a shock hazard to the patient or to medical personnel in the area.

Figure 3:
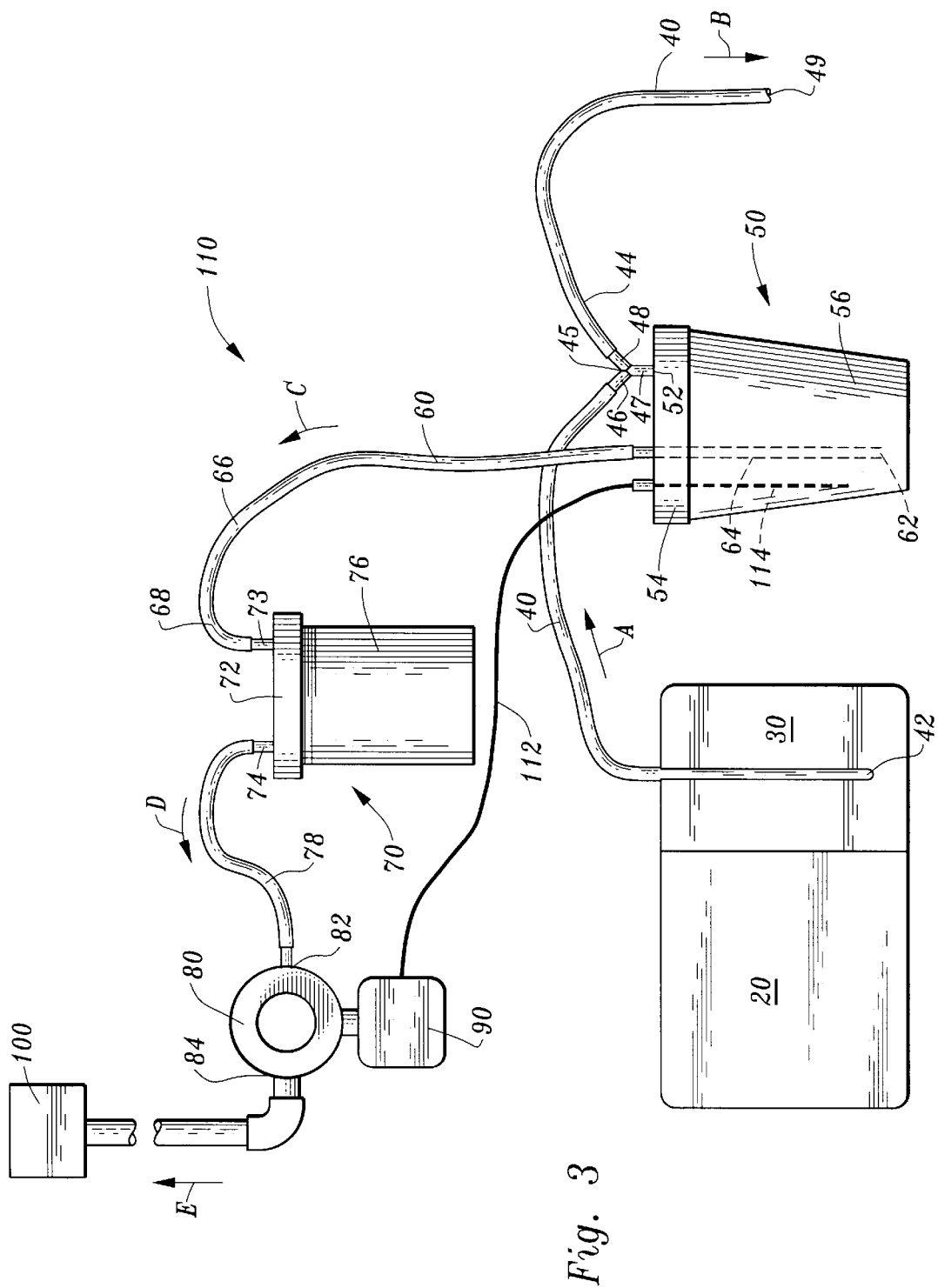
FIG. 3 is a schematic of an optional version of this invention that includes a liquid level sensor in the water trap.

With particular reference to FIG. 3, details of an alternative system 110 which includes a liquid sensor in the form of a water level probe 114 is described. The alternative system 110 is configured similarly to the system 10 of the preferred embodiment. However, the alternative system 110 additionally includes a sensor line 112 coupled to the controller 90 and having a water level probe 114 coupled to the sensor line 112 and located within the water trap 50. The water level probe 114 is configured to detect the presence of liquid and send a signal along the sensor line 112 to the controller 90. Preferably, the water level probe 114 is positioned at a desired maximum liquid level within the water trap 50. When liquid is detected adjacent the water level probe 114, this indicates that the water trap 50 is full up to the maximum desirable level. The signal from the water level probe 114 passes along the sensor line 112 to the controller 90. The controller 90 then automatically causes the valve 80 to toggle from the second closed position to the first open position for the duration manually selected by the user. In this way, the alternative system 110 only comes on when the water trap 50 is becoming dangerously full.

The water level probe 114 would typically be in the form of a single point probe at the maximum desirable level for liquids within the water trap 50. Alternatively, the water level probe 114 can be configured with multiple point probes at different heights within the water trap 50 with some point probes located adjacent the bottom of the water trap 50 and other point probes located near an upper end of the water trap 50. In this way, some portions of the water level probe 114 would signal the controller 90 to cause the valve 80 to toggle from the second closed position to the first open position, namely when point probes of the water level probe 114 detect that the liquid level is high within the water trap 50; and keeps the valve 80 in the first open position until other point probes of the water level probe 114 no longer detect liquid present at the bottom of the water trap 50, at which time the water level probe 114 signals the controller 90 to toggle the valve 80 from the first open position to the second closed position. With such a multi-position water level probe 114 within the water trap 50, the alternative system 110 can adapt both the frequency and duration of operation of the valve 80. In this way, suction is never unnecessarily drawing air out of the ventilator 20 and away from the patient. Rather, the valve 80 always remains in the first open position only for the duration necessary to evacuate the water trap 50, and no longer.

This disclosure is provided to reveal a preferred embodiment of the invention and a best mode for practicing the invention. Having thus described the invention in this way, it should be apparent that various different modifications can be made to the preferred embodiment without departing from the scope and spirit of this disclosure. For instance, the system 10, 110 could be adapted to work both on water traps 50 located along inhalation air supply lines 40 and analogous exhalation air removal lines. When structures are identified as a means to perform a function, the identification is intended to include all structures which can perform the function specified.

What is claimed is:

1. A system for automatically emptying liquids from a ventilator water trap, the system comprising in combination:
   a suction line having a first end inside the water trap and a second end coupled to a canister;
   a valve interposed between a vacuum source and the canister, said valve having at least two positions including a first open position and a second closed position; and
   a timer coupled to said valve, said timer programmed to automatically or manually toggle open and close said valve to said first open and second closed positions when a predetermined amount of time has elapsed.

2. The system of claim 1 wherein said first open position has sufficient time to remove a majority of liquids within the water trap through said suction line.

3. The system of claim 1 wherein said valve remains in said second closed position and only toggles to said first open position by said timer when said predetermined amount of time has elapsed.

4. The system of claim 3 wherein a frequency with which said timer toggles said valve from said second closed position to said first open position is adjustable manually by a user.

5. The system of claim 4 wherein a duration for which said valve remains in said first open position is manually adjustable by a user.

6. The system of claim 1 wherein the canister is located between said valve and the water trap along with said suction line.

7. The system of claim 1 wherein a liquid sensor is located within the water trap at a height within the water trap corresponding with a maximum desirable height for collection of liquids with the water trap, said liquid sensor coupled to said valve in a manner causing said valve to toggle to said first open position when said liquid sensor detect liquids adjacent said liquid sensor.

8. The system of claim 7 wherein said first open position has sufficient duration to allow liquids within the water trap to be removed through said suction line;
   wherein said valve remains in said second closed position and only toggles to said first open position by said timer when said predetermined amount of time has elapsed;
   wherein a frequency with which said timer toggles said valve from said second closed position to said first open position is adjustable manually;
   where a duration for which said valve remains in said first open position is manually adjustable by a user; and
   wherein said canister is located between said valve and the water trap along said suction line, said canister has a volume of two quarts and the water trap has a volume of five ounces.

* * * * *